(12) United States Patent
Bartha

(10) Patent No.: US 8,663,167 B2
(45) Date of Patent: Mar. 4, 2014

(54) DEVICE FOR DELIVERING LIQUID MEDICAMENT

(75) Inventor: Istvan Bartha, Järfälla (SE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 236 days.

(21) Appl. No.: 13/259,473

(22) PCT Filed: Mar. 19, 2010

(86) PCT No.: PCT/SE2010/000065
§ 371 (c)(1),
(2), (4) Date: Dec. 21, 2011

(87) PCT Pub. No.: WO2010/110712
PCT Pub. Date: Sep. 30, 2010

(65) Prior Publication Data
US 2012/0136306 A1    May 31, 2012

(30) Foreign Application Priority Data
Mar. 24, 2009 (SE) ....................... 0900371

(51) Int. Cl.
*A61M 37/00* (2006.01)
(52) U.S. Cl.
USPC ........................................ 604/154
(58) Field of Classification Search
USPC ........................................ 604/154
See application file for complete search history.

(56) References Cited

U.S. PATENT DOCUMENTS

| | | | |
|---|---|---|---|
| 2002/0077601 A1* | 6/2002 | Kawagishi et al. | 604/224 |
| 2005/0004529 A1 | 1/2005 | Veasey et al. | |
| 2005/0154347 A1* | 7/2005 | Neracher | 604/68 |

FOREIGN PATENT DOCUMENTS

| | | |
|---|---|---|
| EP | 1579881 A1 | 9/2005 |
| EP | 1974760 A1 | 10/2008 |
| EP | 2014323 A1 | 1/2009 |
| WO | 03099357 A1 | 12/2003 |
| WO | 2004006998 A1 | 1/2004 |
| WO | 2008155144 A1 | 12/2008 |

OTHER PUBLICATIONS

Form PCT/IB/326, Notification Concerning Transmittal of International Preliminary Report on Patentability.

* cited by examiner

*Primary Examiner* — Jason Flick
(74) *Attorney, Agent, or Firm* — McDonnell Boehnen Hulbert & Berghoff LLP

(57) ABSTRACT

The present invention relates to a device for delivering a fixed dose or an adjustable dose of liquid medicament to a patient. Characterising for the present invention is that it is equipped with a planetary gear with the purpose of increasing the power needed to deliver liquid medicament out of this type of devices. On almost all of the devices of this type appearing on the market with the purpose of delivering a fixed dose or an adjustable dose of liquid medicament, the dose volume can be set in separated steps. With assistance of a planetary gear these steps, which each represent an increase of the volume of the medicament to be delivered, get smaller, which increases the possibility to set an optimum dose volume of the medicament. In its primary field of use the invention is intended to be used together with an injection needle. The invention facilitates to create high fluid pressure in the medicament and can be used to operate an inhaler or a needle free injector at the same time as the invention will keep a compact outside measurement.

20 Claims, 7 Drawing Sheets

DEVICE FOR DELIVERING LIQUID MEDICAMENT

CROSS REFERENCE TO RELATED APPLICATIONS

The present application is a 35 U.S.C. 371 National Application of PCT/SE2010/000065 filed Mar. 19, 2010, which claims priority to Swedish Patent Application No. 0900371-6, filed Mar. 24, 2009, the entire contents of which are incorporated entirely herein by reference.

TECHNICAL AREA

The present invention relates to a device for distribution of a fix dose or a variable dose of liquid medicament to a patient. The present invention is characterized by that it is equipped with a planetary gear with the purpose of increasing the power needed to deliver liquid medicament out from this type of devices in order to avoid using a clumsy mainspring, expensive special made springs such as clock springs or very powerful compression springs in which the stored spring force occasionally exceeds 50 N. An example of this is patent: WO 2008/155144 A1. The planetary gear used in the present invention provides an other advantage, as it lowers the angular velocity which results in that more precise and smaller dose steps can be achieved than by using conventional injectors. In the first place the invention intend to be used in combination with today existing and standardized glass containers for liquid medicament, as for example a cartridge, which is a glass container with an open bottom, with a rubber piston, known as the plunger, which seals the open bottom portion of the cartridge. Furthermore the cartridge also comprises an opening in the front portion, which is sealed by a lid equipped with a hole equipped with a soft partition wall which in most cases is penetrated by the rear side of an injection needle in order to create a fluid duct from the medicament to the outside. As a result of when the user turns a dose knob, which is attached on the backside of the device, a numerical value is changed in a window which indicates the amount of medicament the user intends to deliver. Simultaneously a mainspring in the device will be set to a charged state which is kept in this state by a ratchet mechanism arrangement which is integrated in the device. When the dose is prepared to be delivered to the body the user activates a trigger button which is connected to the ratchet mechanism which then is released, whereby the pre-set mainspring through mechanical components in the device is allowed to push the plunger ahead a certain pre-determined distance with a dimensioned and predetermined force. That the entire dose is delivered is indicated by that the numerical value in the window now displays a start position, which for example could be the numerical value "0".

In most of the competing devices a manually applied force is used to accomplish a plunger transportation ahead, where the user usually creates this force by his/her thumb. Nevertheless there are a few mainspring operated devices on the market. Like the competing inventions the present invention follows the guidelines stated in the international standard for pen-injectors ISO 11608-1.

TECHNICAL BACKGROUND

Liquid medicament is often injected into the body, where it afterwards is absorbed by the circulatory system. In most cases some kind of syringe is used for this purpose. As there is a multitude of different liquid medicaments, with various viscosity, concentrations and greatly varying dose volumes, within a span from about 5 micro liters doses up to about 800 micro liters doses, there is a multitude of specially designed injectors today, manually operated or equipped with drive mechanisms, which all are adapted for different operation modes. The present invention is designed for, with modest or with no modifications, to be applicable for most of occurring operation modes where an injector with an adjustable dose setting arrangement is used.

Most injectors have in common that they are either equipped with an injection needle which is fixed in the medicament container or equipped with a separate injection needle which is described in the international standard ISO 11608-2, where the exchangeable needle can be screw fitted onto the injector or syringe. In the text below "front side" or "front" refer to the end of the injector which contains the injection needle. "rear side" or "back" refer to the opposite end, which in most cases is composed of a dose knob as in the accompanying illustrated embodiment, or by another arrangement for setting the dose volume which the user intend to inject.

The simplest embodiment of a syringe is a completely manually operated syringe, which most important constituent elements are a tubular needle, which is referred to as the injection needle, a transparent medicament container which in most cases is transparent and equipped with a graded scale which purpose is to indicate the amount of medicament which has been injected into the body. At the upper portion of the syringe there is a rod, referred to as plunger rod, which is equipped with a thumb grip at the top, to make it possible for the user to apply a pressure onto the plunger rod. At the front end the plunger rod is attached to a piston, referred to as plunger or stopper which runs inside of the medicament container. By applying a pressure on the plunger rod, the plunger moves forward in the medicament container, whereby the enclosed medicament passes out through the tubular needle.

A regular type of syringes are the ones known as insulin pens (pen-injector). These are, among other patients, also used by diabetics, some times on several occasions per day. In most cases the insulin is kept in a medicament canister, also known as a cartridge. A cartridge is a glass- or plastic canister which in the front end is sealed by a special cap. This cap comprises a hole in it's front end which normally is sealed by a elastomeric cloth septum) mounted on the inside of the cap. Standardized cartridges are very commonly used by the pharmaceutical industry and often apply to the international standard ISO 11608-3 which also facilitates the FDA-approval of the finished product. There are several companies which produces pen-injectors, which results in that the pen-injector could be designed in a multitude of ways. Nevertheless there is an international standard, ISO 11608-1 which describes certain standard demands which a pen-injector must fulfil, and furthermore this standard states guide lines for the design of the pen-injector. This standard also puts minimum requirements on which quality and repeatability regarding the dose setting that the pen-injector has to fulfil. Typically regarding a pen-injector is that the user sets the requested dose volume by operating a dose knob which is placed on the back end of the pen-injector body, whereby the set dose volume is displayed as a numerical value in a window placed somewhere along the pen-injector body. Also typical for many of the manually operated pen injectors is that the dose knob, when it is turned, protrudes backwards out of the pen-injector body with a turning movement. As the proper dose value is set, which is verified by that the correct numerical dose value is displayed in the window, the user penetrates the injection site on the body, for example the thigh or the stomach, with the injection needle. Thereafter the user pushes his/her thumb against the dose knob whereby the dose knob is pushed back into the pen-injector body again. As the dose knob is directly or indirectly mechanically connected to the plunger rod, thus the preset volume of liquid medicament is injected into the body. A verification of that the injection is completed is that the dose scale in the window again indicates start position, which can be indicated by a "0" or by another symbol.

There is a multitude of liquid medicaments, and insulin is a typical example of a liquid medicament. Other examples of liquid medicaments are growth hormone or FSH, which is used to support human reproduction. Botox® is yet another example of a liquid medicament. All medicaments consist of unique chemical compositions, concentrations and characteristic dose sizes measured in for example μl (micro liters) or some other dose scale, depending on how the dose volume is represented.

In some cases the pharmaceutical manufacturer states a weight unit for the active substance which can be dissolved in a liquid and by a varying concentration. Therefore, in this case it is the amount of active substance which decides how the measurement of the dose will be represented. Furthermore the viscosity fluctuates between different liquid medicaments. As an example Botox® has a high viscosity.

The viscosity is also in many cases temperature dependent, which results in that medicaments stored in a refrigerator are more viscous than the same medicament stored in room temperature.

In many cases a single medicament container (cartridge) is used for repeated treatments. As an example a cartridge with a volume of 3 ml. containing insulin is sufficient for up to one months use, depending on the size of the doses the patient need to inject and how often the doses are administered. Because of the risk of bacterial growth on the needle which can spread into the medicament through the needle duct, a system of exchangeable needles is used for insulin. It is recommended to change the needle after each injection. The same system with exchangeable needles is also used for many other types of medicaments.

The variable dose sizes result in that the rear portion of the dose knob (which will be pushed into the injector body) will move to different positions behind the injector body when the dose is set, which corresponds to the present dose volume, i.e. the pitch fluctuates.

The patient experiences more or less pain by pricking him/herself with an injection needle, which also, if needles are frequently used, can result in tissue damages at the injection site, which also is well known among diabetics, and therefore the needle manufacturers continuously strive to develop thinner needles.

Even if it's stated that new, thinner injection needles hold the same flow resistance as older, thicker injection needles, practical tests show that the flow resistance tend to increase, the thinner the cross section area gets on new and on future injection needles. Practically, this means that a higher force must be applied on the plunger rod when using future thinner injection needles in order to expel medicament from the medicament container. In those cases where the patient has a restricted nimbleness or strength in his/her hand this is regarded as a limitation. It is often strived for that the patients shall administer the injection of the medicament on their own. As an example, this could result in that children with small hands who inject a large dose of growth hormone experience outright ergonomic difficulties, if they use one hand to grasp around the injection site, that is the body tissue, between one hands thumb and pointing finger, and with the other hand push in the dose knob. This is also an argument for that automatic devices designed for distribution of liquid medicament, which use a mainspring, electric motor or gas container or some other type of accumulated source of power for driving a plunger rod, will increase their market share on the expense of manually driven plunger rods.

A third type of pen-injectors is a pen-injector where the user, by turning a dose knob, which in most cases is placed on the rear end of the injector body, sets the desired dose volume to be distributed, and simultaneously, through the dose knob applies a load on the spring, which in it's turn propels the plunger rod as the medicament is injected into the body. An example of this is the Autopen (trademark).

Usually occurring sources of power for driving a plunger rod are the ordinary helical compression springs made of steel wire with spring characteristics, torsion springs or clock springs, which are either thin- or narrowly tied clock springs (known as motor springs) of different versions. These springs have in common that they work within an interval and that these springs are stored in a preset state. The reason for this is that through the whole injection course, there must be sufficient power in the spring to overcome the internal power losses such mechanical friction, flow resistance and also the maximum allowed time for an injection.

BRIEF DESCRIPTION OF THE DRAWINGS

Present invention will be described by a concrete and illustrative design solution which provides an advantageous embodiment of the actual invention. Components, of which the present invention is composed, can be designed in more than one way, and for that reason the invention will further be referred to as "described embodiment". This described embodiment is illustrated by these enclosed figures in which also reference numbers referring to parts referred to in the patent text are presented.

BRIEF DESCRIPTION OF THE INVENTION

Figure 1:
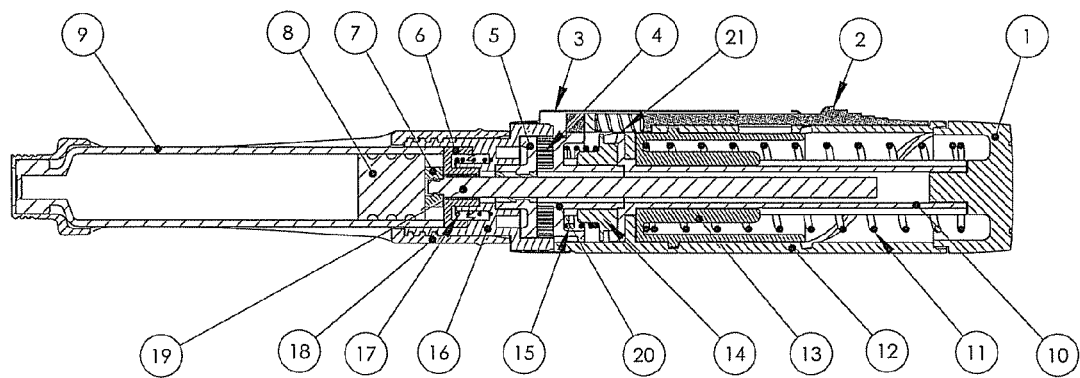
FIG. 1 illustrates a cross section view of an example of a design solution of the invention, and on the present design solution belonging designed parts. Naturally the number of parts can be decreased when the invention is prepared for production, but this design solution comprises all functions, and the design of mechanical solutions which characterizes the present invention.

The present invention relates to a device which assisted by a mainspring, distributes liquid medicament to the body, via an injection needle as a liquid or via a mouth piece which converts the liquid medicament to a spray. The invention, see FIG. 1, comprises a cover which in this embodiment comprises a front cover (16) and a rear cover (12), a drug canister wherein the liquid medicament is stored which in the described embodiment comprises of a cartridge (9) with adherent plunger (8), which in the front end is enclosed by a lid equipped with a septum, which constitutes a separation wall which could be penetrated by an injection needle, and thus create a sealed fluid duct from the cartridge to the injection needle.

The liquid medicament is distributed by a plunger rod (19) with a supported spinner (7) transport the plunger (8) ahead towards the injection needle, whereby the liquid medicament which is put under overpressure is squeezed through the hole of the injection needle. Depending on the requested amount of drug to dose, i.e. the dose volume, the plunger rod (19) moves forward a predestined distance inside the cartridge. This forward movement will from now be denominated as the pitch. Thus the dose volume is equal to the pitch multiplied with the cross section area of the plunger (8). The plunger rod (19) is equipped with threads and is screwed ahead a certain parts of a full turn, which depends on which dose volume the user previously has set by a dose knob (1). The plunger rod (19) is also equipped with longitudinal tracks or alternatively flat longitudinal surfaces, at least on one side but in most cases along both sides, where the normal distance between the sides is less than the maximum diameter on the plunger rod (19).

The dose knob (1) is firmly locked to a drive shaft (10). The inside of the drive shaft (10) is shaped as a longitudinal tube, wherein the plunger rod (19) can move freely. The rear portion of the drive shaft (10) is equipped with longitudinal tracks arranged as a spline. A dose drum (13) is equipped with longitudinal flanges which can move freely along the longitudinal spline-shaped grooves in the drive shaft (10). By turning the dose knob (1) the dose drum (13) will rotate simultaneously. As the outer surface of the dose drum (13) is equipped with a thread which runs inside of threaded grooves in the rear cover (12) the dose drum (13) is also forced to spin backwards towards the dose knob (1). Furthermore, the dose drum (13) is equipped with numerical values, where each value represents a certain preset dose volume. Through a window opening in the rear cover (12), the currently valid numerical value on the dose drum (13) can be read by the user, and as the mechanism inside of the automatic injector is fully synchronized a certain visible numerical value always represents a certain plunger rod pitch. A mainspring (11) is compressed synchronously to that the dose drum (13) rotates in reverse direction towards the dose knob (1). When the user has set the requested dose volume the device will be in an active state of rest. This implies that the compressed spring (11) is locked in a loaded state. This is accomplished by integrating a ratchet wheel in a front end of the drive shaft (10), which can be seen clearly in FIG. 1, which at the wind up procedure acts together with a clutch mechanism (14) and a clutch return spring (15). The clutch (14) is simply a ratchet mechanism, which in this embodiment is arranged in a longitudinal and cylindrical configuration. The clutch (14) lets the drive shaft (10) rotate in one direction as oncoming teeth flanks are leaning in this direction of rotation, and as the user easily by manually applied power can overcome the axial and reverse directed axial clutch return spring force (15). In the blocked rotational direction the contact surfaces between the clutch teeth and the ratchet teeth on the drive shaft (10) are vertical in the axial direction and the resulting force which pushes the clutch ahead is negligibly small.

In order for the above described ratchet arrangement to work, the clutch (14) is unable to rotate, but only to be able move in it's forward direction and thus jump over the ratchet wheel surface which is equipped with teeth. This is accomplished by equipping the clutch (14) with longitudinal spline grooves, or alternatively protruding spline features, which run in corresponding spline arrangement in a dose stop (20).

The clutch return spring (15) which pushes on the clutch (14) with a backward directed force ensures that the clutch (14) and the ratchet wheel teeth on the drive shaft (10) are always connected to each other. As the clutch (14) is locked from rotating relatively to the dose stop (20) which in it's turn is locked from rotating relatively to a trigger button (2) it is possible to set the dose, and thereafter the user will be ready to release the dose stop (20), which in the illustrated embodiment implies that the user pushes the trigger button (2) ahead whereby the liquid medicament is delivered through the injection needle.

As the user delivers a dose of the liquid medicament, according to above mentioned procedure, the user releases the dose stop (20), which is showed in the illustrated embodiment, by pushing the trigger button (2) ahead towards the cartridge.

The preset mainspring (11) is again allowed to expand ahead, whereby the dose drum (13) rotates towards its initial start position, and by the spline connection connecting the dose drum (13) to the drive shaft (10) transfers the torque to the drive shaft (10). The drive shaft (10) transfers the torque to a planetary gear mechanism through the clutch (14) and the dose stop (20).

It is possible to configure a planetary gear mechanism in many different ways. In the present invention an outer ring gear is locked and integrated in the front cover (16). A front end of the dose stop (20) is equipped with a sun gear, which transfers the torque to a planet carrier (5) through two or more planet gears (4) which are assembled on the planet carrier (5). Regardless of the number of planet gears (4) the theoretical gear ratio between the sun gear and the planet carrier (5) will remain unchanged.

A hub of the planet carrier (5) is either shaped as a nut, with threads corresponding to the plunger rod threads, or as a round axially protruding hole equipped with longitudinal flanges or flat surfaces, where the normal distance between the surfaces is less than a maximum diameter of the plunger rod (19). In the embodiment where the planet carrier hub is shaped as a nut, a hub of a plunger rod clutch (6) is shaped as a round axially protruding hole equipped with longitudinal flanges or flat surfaces, where the normal distance between the surfaces is smaller than the maximum diameter of the plunger rod (19). In this case the planet carrier threads rotate, while the plunger rod clutch (6) is locked. In this embodiment the plunger rod (19) is driven ahead in a linear movement and pushes the plunger (8) in front of itself whereby liquid medicament is delivered out of the cartridge (9), provided that an injection needle is screw fitted or snapped onto the front end, which open up a fluid duct for the medicament. Otherwise the liquid pressure raises until all elastic components, as for example potential air bubbles, are compressed. Thereafter the longitudinal forward directed movement of the plunger rod (19) ceases.

In the second embodiment, in which the planet carrier hub is equipped with a round, axially protruding hole with longitudinal flanges or flat surfaces, and where the normal distance between the surfaces is less than the maximum diameter of the plunger rod (19), the planet carrier rotates in the same way as in the previous embodiment described above. In this embodiment the torque is not transmitted through the threads, instead it is transmitted via the longitudinal flanges or flat surfaces to the plunger rod (19), which thus is forced in rotation. In the second embodiment the hub of the plunger rod clutch (6) is equipped with a thread which is kept still. In this embodiment the plunger rod (19) moves ahead with a forward directed rotation.

These two embodiments can be compared to, in the first embodiment, to tighten a nut onto a screw which is kept still, and in the second embodiment, to tighten a screw into a fixed nut. The relative movement between the screw and the nut is the same in both cases. In the first case the force is transferred from the nut to the screw, and in the second case the force is transferred from the screw to the nut. Both procedures are similar to each other, and neither of the procedures has any direct advantages or disadvantages compared to the other.

Consequently, the planet carrier (5) in the above described device transfers the torque from the drive shaft (10) via the clutch (4) and dose stop (20 to the plunger rod (19), either by having a hub equipped with threads and thereby screw the plunger rod (19) forwardly, or by having a hub with longitudinal flanges which transfer the torque whereby the plunger rod (19) rotates forwardly through a fixed thread which is integrated in the plunger rod clutch (6).

DETAILED DESCRIPTION OF THE INVENTION

In the present detailed description, the terms "front side" or "front" and "rear side" or "rear" are used to define the direction of different components. In the following text, "front side" or "front" refer to the physical end of the invention where the medicament is delivered out from the device, and also constitutes the end where an external component can be connected onto the device. It could be an injection needle, which is screwed fitted or snap-locked onto the device, or a mouth piece which transforms the pressurized liquid medicament into a spray or an aerosol. It could also be another kind of orifice, as for example a component equipped with a hole, which is pressed against the skin, where the fluid pressure of the liquid medicament is sufficiently high to enable the liquid to penetrate the patient's skin without using a penetrating needle, whereby the device in this embodiment constitutes a needle-free injector for medicament. In the following text, "rear side" or "rear" refer to the physical end of the invention which is equipped with a dose knob (4) which is illustrated by the figures.

The device for distribution of liquid medicament which is illustrated by the figures, comprises a cover consisting of the rear cover (12) and the front cover (16). In the described embodiment these two covers (12, 16) are joined together by snap-in closures. In other embodiments, the covers (12, 16) could be ultrasonically welded, glued, heat staked, riveted or screw fitted together. It is convenient to mould these parts of plastic, as for example of polycarbonate, cycoloy (trademark) or ABS but the covers could also be manufactured of metal, as for example of brass or steel.

In the described embodiment the joint is further reinforced with a deep drawn piece of sheet metal shaped as a barrel ring (3) which also consists of a protrusion directed towards the rear side of the device. This piece of sheet metal, as for example stainless steel, can be replaced by a moulded feature made of plastic, as for example of LCP.

Figure 5:
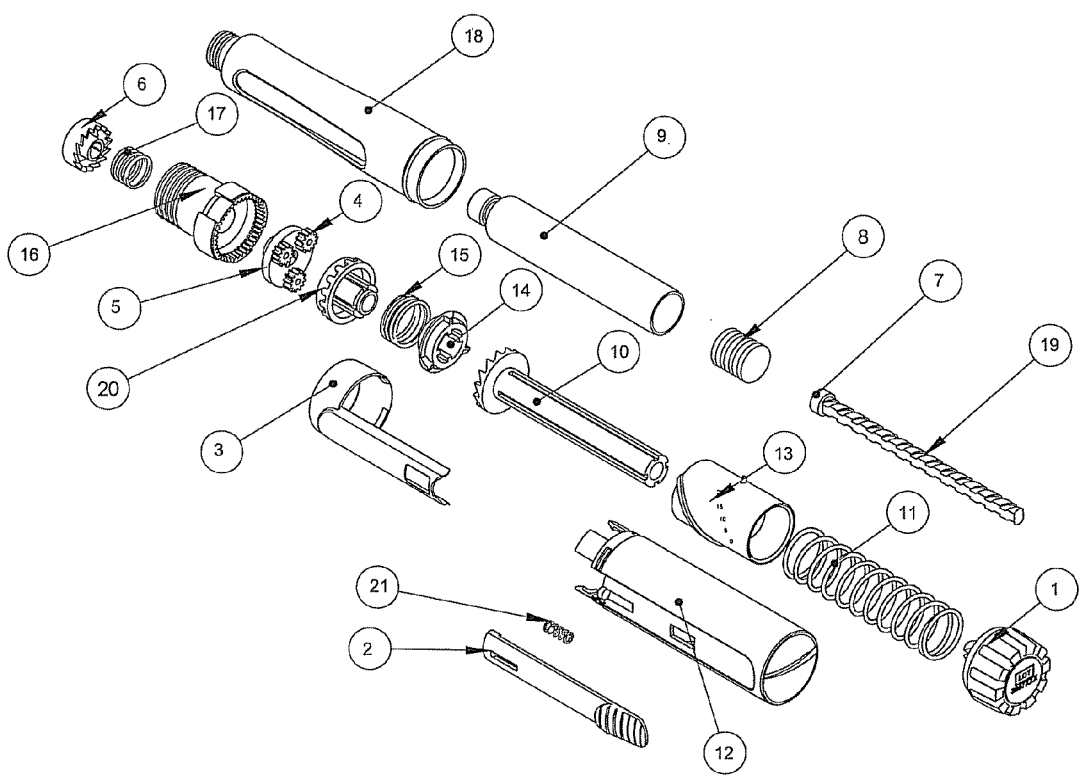
FIG. 5 illustrates an exploded view of the design solution which also is illustrated in FIG. 1.

The ring (3) does not only function as a reinforcement of the joint between the front cover (16) and the rear cover (12), it also hides the joint and furthermore guides the trigger button (2). The trigger button (2) serves two purposes, the main function is to act as a trigger, which implies that the user separates the stop features along the perimeter of the dose stop (20) by pushing the trigger button (2) towards the front end of the device, and by this allows the inner components to rotate freely. This phase is executed when the user intends to deliver the liquid medicament. It is preferable to manufacture the trigger button (2) of transparent plastic, as for example of transparent polycarbonate, as the rear protrusion of the trigger button (2) can be used as a window for numerical values which are placed along a helical track along the outer surface of the dose drum (13) which is shown by FIG. 5. The trigger button (2) could also be made of metal or of another plastic material. In this case the position of the numerical values placed on the dose drum (13) has to be shifted, either by shifting the trigger button (2) angularly referred to the longitudinal direction of the device so that the numerical value can be read at the side of the trigger button (2), or else the trigger button could be equipped with a hole in its rear protrusion, through which the user can read the numerical value.

This hole could also in this case be equipped with a separate magnifying glass made of glass or transparent plastic.

Figure 3:
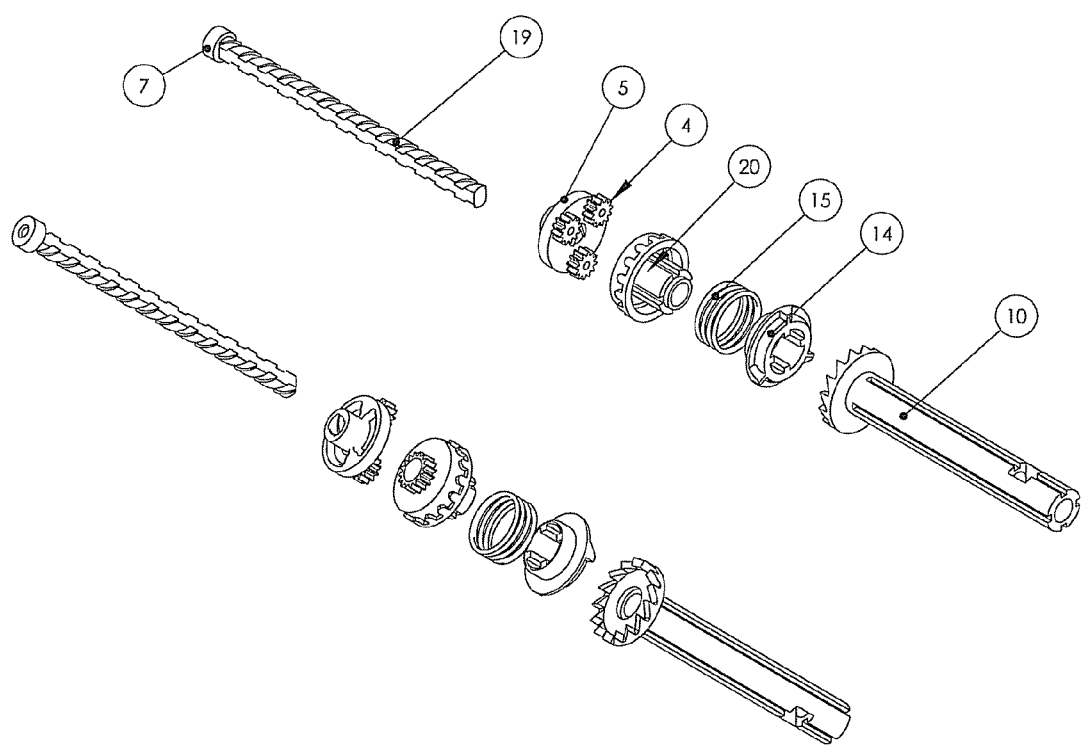
FIG. 3 illustrates two views in perspective, one from the front side view and one from the rear side view showing the drive shaft (10), the clutch (14), the return spring (15) for the clutch (14), the dose stop (20), the planet carrier (5) with three assembled planet gears (4) assembled and the plunger rod (19) with a snapped-on spinner (7) where the geometric shape of each component can be seen.
Figure 4:
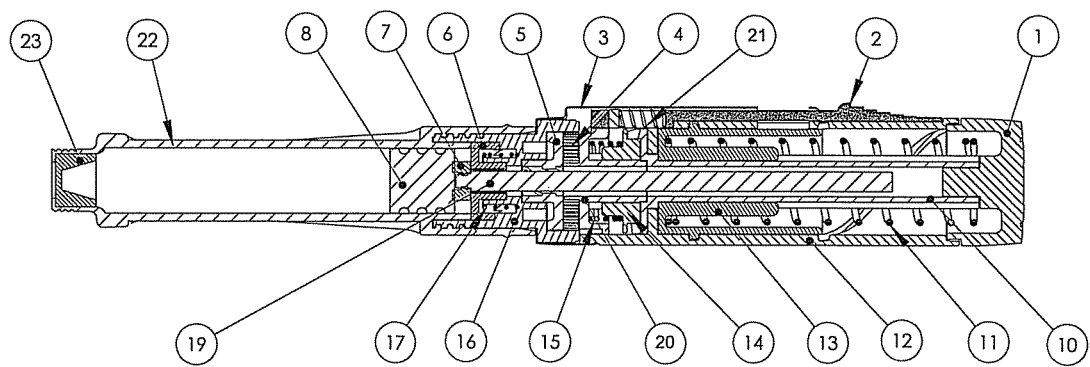
FIG. 4 illustrates a cross section view of an example of a design solution of the invention, where the cartridge is integrated in the cartridge housing (22) which inside also is equipped with a septum (23). In other respects the design solution is identical to the embodiment illustrated in FIG. 1, FIG. 2, FIG. 3 and in FIG. 5.

The trigger button (2) is shifted against its rear stop position in the non-active mode, and rotationally locks the dose stop (20) as long as the user doesn't push the trigger button (2) ahead. The trigger button (2) is kept in place in its rear stop position by a trigger spring (21) which front end in the illustrated embodiment pushes against a surface in the rear cover (12) and which rear end pushes against a recessed surface in the trigger button (2). This way a force which is directed towards the rear is created, which is used to ensure that the dose stop (20) is locked. When delivering a dose the trigger button (2) is pushed forwardly whereby the dose stop (20) is released. In FIG. 3 the dose stop (20) is shown from a front side view and a rear side view. The dose stop (20) is hollow in its longitudinal direction, with a diameter of the hole which exceeds the maximum diameter of the plunger rods cross-section. The dose stop (20) is equipped with a backward directed end of a shaft which is equipped with spline grooves in which the clutch (14) can move back and forth. Furthermore the dose stop (20 is equipped with an outer ring which on its outer surface is equipped with evenly distributed stop features, which together with corresponding stop features on the front end of the trigger button (2) constitute a trigger function, or in other terms, a rotational lock which can be operated by the user.

Figure 2:
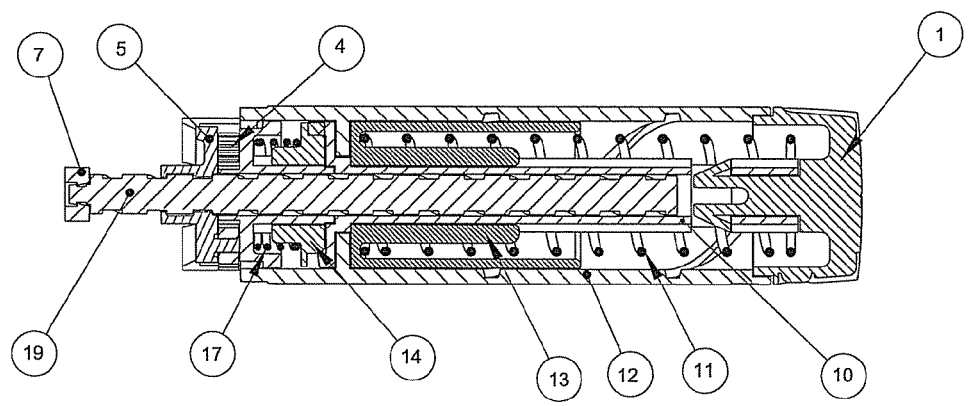
FIG. 2 illustrates an enlarged detail view of the cross section view in FIG. 1, where the design of the mainspring which drives the plunger rod, and the power transmission to the drive shaft (10), the clutch mechanism (14), the return spring (15) for the clutch (14), the dose stop (20) and the components that are comprised in the planetary gear are shown in detail.

The rear cover (12), which is illustrated by FIG. 2, is equipped with one or more threaded tracks propagating on the inside in a spiral shaped pattern, and thus constitute an internal thread. The number of tracks depend on if the thread has one or more entrances. The dose drum (13) is equipped with corresponding external threads which correspond to the internal threads which are integrated in the rear cover (12). The dose drum (13) is guided by the threaded tracks and rotates backward when the dose knob (1) is turned manually until it finally hits the rear stop position, which in this embodiment is constituted by the dose knob (1). In the same way the dose drum (13) is free to move to a front stop position, which in this embodiment is constituted by the front end of the internal threads in the rear cover (12). This consequently constitute a front stop position for the forward movement of the dose drum (13). Another way of creating a front end stop position for the dose drum (13) movement is to equip the rear cover (12) with a protruding feature or separation wall which also would constitute a stop.

The dose drum (13) also rotates by a window, or a hole in the rear cover (12). As the dose drum (13) is equipped with pre-defined stable positions, which are synchronized to the stop positions in the clutch (14) the dose drum (13) can be equipped with numerical values along its outer surface. These numerical values are grouped along a spiral shaped imaginary curve with the same pitch as the external thread of the dose drum (13). This imply that a certain movement and synchronized backward turn of the dose drum (13) will always result in that a certain numerical value will be displayed in the window. This numerical value indicates the size of the dose of the liquid medicament which the user of the device intends to deliver. In another embodiment of the invention the inner wall of the rear cover (12) could be equipped with an external thread which in that case correspond to a recessed thread in the dose drum (13).

The dose drum (13) is preferably made of plastic, as for example of ABS, but it can also be made of metal, as for example of brass. The advantage by using plastic is that the material can be coloured, for example with white paint to increase the contrast between the background, consequently the outer surface of the dose drum (13), and the numerical values which either are printed, as for example by using tampon print, or consists of a decal applied on the outer surface, as for example by in-mould decoration or marked by using jet-printing technique or laser printing technique, should be as good as possible. This is important, particularly if a diabetic will use the device, who often suffer from impaired eyesight, as a consequence of the decease.

The dose drum (13) is in its longitudinal direction equipped with a hole inside of which the drive shaft (10) can move freely in the longitudinal direction of the device. By designing the hole with a spline function, which in this embodiment imply longitudinally protruding grooves and equip the drive shaft (10) with corresponding longitudinal grooves, a torque can be transferred from the dose drum (13) to the drive shaft (10).

The drive shaft (10) is hollow and has an internal diameter which exceeds the maximum diameter of the plunger rod (19). This implies that the plunger rod (19) can move freely along the longitudinal direction of the internal hole of the drive shaft (10). At the rear side of the drive shaft (10) the dose knob (1) is firmly attached.

The dose knob (1) is operated by the user, in that way that the user turns the dose knob (1) until the correct numerical value is displayed in the window in the rear cover. In the illustrated embodiment the front portion of the dose knob (1) is equipped med snap-in closures. The dose knob (1) transfers a torque from the hand of the user to the drive shaft (10). As the mainspring (11) is preset, the dose is preset which implies that the dose knob (1) is not free to rotate in relation to the drive shaft (10). Therefore, in the present embodiment of the invention the dose knob (1) is equipped with snap-in closures which together with corresponding holes in the rear portion of the drive shaft (10) locks the dose knob (1) in the longitudinal direction and simultaneously allows torque transmission to the drive shaft (10). Alternative ways of locking the dose knob (1) against the drive shaft (10) is by joining them together by using ultrasonic welding, gluing or heat staking. These parts can also be press fitted, if one of these parts is equipped with small protruding edges, with the height fluctuating from 0.1 mm up to 0.3 mm and which will deform as the two parts are pressed together.

When the user turns the dose knob (1) the mainspring (11) will accumulate the load and thereby store the force necessary for the device to be able to deliver the liquid medicament as the user pushes the trigger button (2) ahead and thereby releases the dose stop (20). In this embodiment of the invention the mainspring (11) is a regular spiral shaped compression spring with a round cross section profile of the spring wire. The cross section profile of the wire could also be rectangular or some another shape. The material used for the spring (11) could for example be resilient stainless steel or resilient regular steel. Most of the automatic devices for delivering liquid medicament available on the market today use some type of spring unit to create the force needed to distribute liquid medicament. One example of the most common spring types are the clock springs either wound with distance between the coils or tightly wound and made of a flat helical sheet metal strip. Another example is a compression spring which is used in the present invention as a source of energy. Yet another example of a mainspring (11) is some type of torsion spring. These springs have in common that their force/compression curve for linear springs, and respectively the force/angular turning for radial springs can be regarded as more or less linear within the active operation interval for the spring.

Regarding automatic devices for distribution of liquid medicament, in all existing embodiments there are a number of factors which result in an inherent friction in all devices, and thereby a friction force which has to be exceeded by the mainspring. Furthermore it is widely known within the pharmaceutical industry that plungers many times stick to the glass surface of the cartridge, which in some cases depend on that the surface pressure between the plunger and the glass in course of time presses away the silicon treatment which the glass surface has undergone. The force which has to be applied on the plunger, in order to start the movement at all is known as "break-loose" force. Because of all the inner frictions the spring has to, provide at least a minimum force to the plunger rod under the entire distribution phase, or in other terms the dose delivery phase. If this force is less than that, the inherent friction forces will exceed the movement which causes the dose delivery to cease. By this reason all mainsprings are pre-set in such manner that they deliver sufficient force all the way until the dose delivery mechanism stops in the front stop position, which is needed in order to maintain the mainspring in a static pre-set state.

From this static pre-set state the user increases the spring force as he/she turns the dose knob (1) to set the correct dose size.

The drive shaft (10) performs a variety of tasks. Its rear end is, as described above, shaped as a mechanical joint fitting to be able to attach it to the dose knob (1). The rear portion of the drive shaft (10) is equipped with splines for transfer of the torque from and to the dose drum (13). The drive shaft (10) is in its longitudinal direction hollow in order for the plunger rod (19) to run freely on the inside in the longitudinal direction and also be able to rotate freely inside of this hole. On its front end the drive shaft (10) is equipped with a toothed flange which composes a ratchet wheel. The teeth are shaped the same way as the teeth in a regular ratchet wheel, with the top of the teeth pointing ahead in this embodiment. The teeth are designed with one side sloping, which allow the corresponding teeth of the clutch to slide on top of its surface. The opposite side of the teeth are leaned approximately 90 degrees in the normal direction from the bottom of the teethed flange.

This implies that the force transmission between the teeth of the drive shaft (10) and the teeth of the clutch (14) are normal to the plane, which imply that they are rotationally locked to each other in this direction.

The drive shaft (10) could be manufactured of plastic, as for example of polycarbonate with additives such as glass and teflon, but it can also be made of metal, as for example of stainless steel or brass. It is important that the sun gear is rotationally locked to the drive shaft (10) in order to be able to transmit the torque from the drive shaft (10). When the user set the dose which he/she intend to distribute, each tooth in the ratchet wheel corresponds to a dose increment which is indicated as a numerical value in a window in the cover. A tooth corresponds to a certain angular turn, which is transformed to a certain plunger rod pitch by the mechanical parts. The torque created by the mainspring (11) is transferred through the clutch (14) to the dose stop (20) and its sun gear shaped front end via a spline arrangement.

Figure 6:
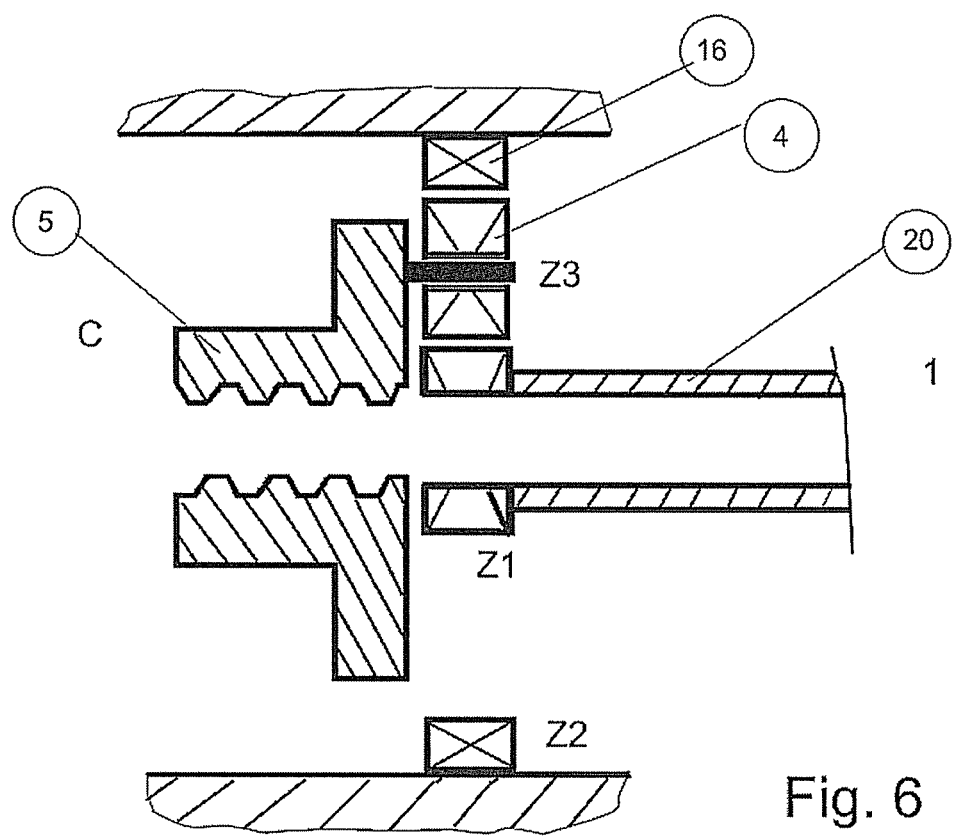
FIG. 6 illustrates a schematic picture of the planetary gear which is used for the present invention. Z1 states the number of (cog) teeth on the sun gear. Z3 states the number of teeth on the planet gears and Z2 states the number of teeth on the fixed ring gear.
Figure 7:
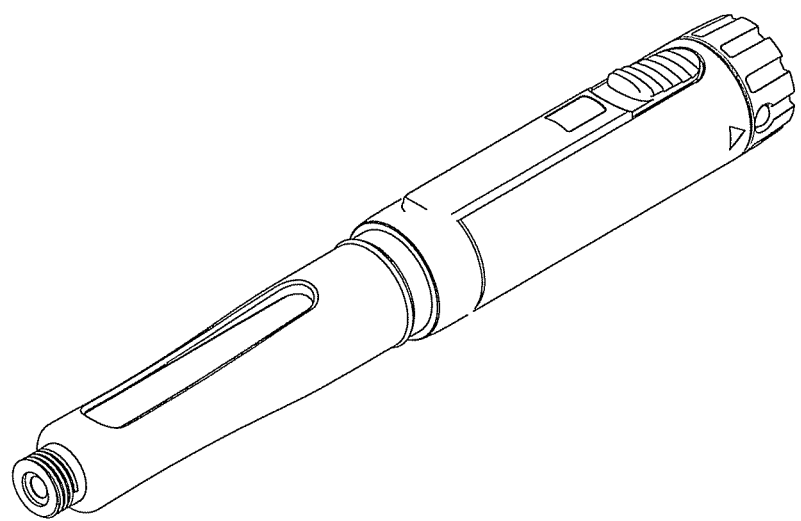
FIG. 7 Illustrates a view of the embodiment which illustrates the invention.

The dose stop (20) with it's integrated sun gear constitutes the input shaft to a planetary gear mechanism. FIG. 6 illustrates the schematic structure of the planetary gear mechanism. The input shaft is represented by the number 1. The planet carrier (5) constitutes output shaft which also is represented by the letter C. A typical planetary gear mechanism consist of an input shaft, 1, equipped with a sun gear, which is equipped with a number of teeth Z1, furthermore a planetary gear mechanism includes of a planet carrier (5) which hub shaft also constitutes the output shaft from the planetary gear mechanism, C. One or more planet gears (4) are assembled on the planet carrier (5) on a certain distance from the hub axis, and they are equipped with a number of teeth Z3.

In the present invention the ring gear on the front cover (16) is kept locked in relation to the sun gear on the dose stop (20) and the planet gears (4). In the present embodiment this is accomplished by integrating the ring gear into the front cover (16). The ring gear is a gear with a number Z2 of teeth pointing toward the hub. Furthermore, in this embodiment the hub hole in the planet carrier (5) is shaped as a nut which drives the plunger rod (19) ahead with a lower gear than the drive shaft (10). In order to attain a forwardly directed plunger rod (19) movement, instead of spinning along with the planet carrier (5), the plunger rod (19) has to be linearly guided either in front of or behind the planet carrier (5). This implies that the plunger rod (19) only has one degree of freedom and is only allowed to move ahead with a linear movement. The linear guide in this embodiment is constituted by a non-circular longitudinally protruding hub hole in the plunger rod clutch (6). The profile of this hole corresponds to a corresponding profile along the plunger rod (19) long sides.

When observing the raw material of a plunger rod it is a threaded rod, with one or more entrances for threads. By removing material from this raw material a non-circular cross section profile can be achieved. The result of the plunger rod (19) movement will be a forward movement and the resulting force in the plunger rod (19) will be directed ahead. Yet another embodiment of this invention is accomplished by shaping the hub hole in the plunger rod clutch (6) is equipped with internal threads, corresponding to the plunger rod threads. In this case the planet carrier (5) is equipped with a longitudinal protruding hub hole with a linear guide which corresponds to the cross section profile of the plunger rod (19). The difference is that in this case the torque is transferred from the planet carrier (5) to the flat recesses along the threaded long sides of the plunger rod (19).

FIG. 5 distinctly illustrates how the plunger rod (19) could be designed. In this embodiment the plunger rod (19) will rotate as it moves ahead. To prevent the plunger (8) from obstructing the plunger rod (19) rotation and thereby increase the resistance which restrains the desired linear movement ahead of the plunger rod a spinner (7) has been mounted in the front end of the plunger rod (19). It constitutes the front end bearing of the plunger rod (19).

In the illustrated embodiment the spinner (19) is snapped onto a flanged shaft journal in the front end of the plunger rod (19).

FIG. 6 illustrates the input shaft, 1, which rotates with the angular velocity ω1. This shaft propel the output shaft, C, which will rotate with an angular velocity ωC. The velocity of the rotation which the output shaft will get also depends on the number of teeth of which the included gears are equipped with, i.e. the number of teeth on the sun gear Z1, the number of teeth on the planet gears Z3, and the number of teeth on the fixed and outer ring gear with internal teeth Z2 with the angular velocity ω2 which accordingly is equal to 0.

The relation between ω1 and ωC is described by the formula:

$$\omega C = \frac{\omega 1}{1 + \frac{Z2}{Z1}}$$

By gearing down the angular velocity several advantages can be obtained. One advantage compared to known technology within the pen injector field is that the today existing injectors, as for example the insulin pens, don't have this type of gear box, which results in that the size of the teeth of the ratchet wheel used in almost all design solutions has to be smaller, if a single dose step is small, or in other terms if the plunger rod is expected to move a very short distance. This put demands on the manufacturing precision when shaping the teeth of the ratchet wheel. This also imply that the wear which takes place between the pawl and the ratchet wheel quickly will wear down the teeth and thereby limit the duration of existing injectors. By introducing a planetary gear mechanism the teeth can have a more heavy-duty shape as the angular speed is geared down, which in present case increases the robustness of the design. If, on the other hand, the fine resolution between the teeth remain about the same as in the now existing injectors, the user will have an opportunity to fine tune the dose volume, which in a concrete example implies that a diabetic, who by a very good understanding of the amount of insulin he/she should inject, will with present invention get the opportunity to further fine tune the dose. If a user today has the opportunity to adjust his/her dose in steps of 5 IU, the planetary gear will make it possible for the user to adjust the dose in steps of 2.5 IU.

Yet another embodiment of the invention is achieved by serially couple two or more planetary gear mechanisms where the outgoing shaft from the first planetary gear mechanism is equipped with a sun gear equal to the sun gear in the front end of the dose stop (20) in order to further gear down the angular velocity, which will enable to set doses as small as 1 IU or less with accuracy, or to achieve an even higher force acting on the plunger rod (19).

The present invention has a great benefit, as the planetary gear mechanism takes up very little space. A device which delivers a fixed or adjustable dose of liquid medicament to a patient should not be bulky, on the contrary it should be easy to fit within the handbag or the jacket pocket. Furthermore the international pen-injector standard ISO 11608-1 states in a regulation that it should "resemble a pen".

Yet another benefit which will be achieved by implementing a planetary gear mechanism is that the plunger rod (6), with unchanged mainspring force is able to deliver a significantly higher force directed ahead to the plunger (8). This implies that the present invention is suitable to use for high viscous liquid medicaments such as BOTOX® and Zoladex® which are high viscous medicaments, at the same time as it will not get bulky, as it doesn't require an extra powerful mainspring. As future injection needles, which are described by the international standard ISO 11608-2, tend to get thinner and thinner the flow resistance in these needles will get higher than the present needles, if the length of the needle is kept constant, which in most cases is 12 mm.

The reasons why the needles get thinner is that frequent users tend to develop scar tissue and damages on nerves at the injection site, and that the pain sensation decreases if the skin is penetrated by a thinner needle. Yet another benefit by using a planetary gear mechanism is that the preset of the mainspring (11) can be reduced which results in that the technical life length of the present invention can be enhanced compared to today existing injectors which are equipped with mainsprings. A factor which often limits the theoretical life length of injectors is the creep behaviour of thermoplastics as they are exposed to static load, as for example by a preset mainspring.

As a consequence of the presence of a planetary gear mechanism in the present invention, consequently a high fluid pressure can be achieved in the liquid medicament, and at the same time keep the outside measurement of the present invention small and handy, and thus be used to transform the liquid medicament to a vapour, also referred to as soft mist. In this field of application the present invention can be used to propel a medicament inhaler where the medicament is stored in the cartridge (9) in liquid state. Finally, the present invention is, due to it's capability of creating a high fluid pressure, usable for injecting medicament straight into the body tissue without the necessity of the use of any injection needle for penetrating the skin, and thus open up a fluid channel for transportation of medicament into the body tissue.

Automatic devices for distribution of liquid medicament, in particular insulin pens, are often divided in either disposable devices or reusable devices. Disposable devices will be referred to as disposable devices, and reusable devices will be referred to as reusable device in the following text.

A concrete example of a disposable device is a disposable insulin pen. A disposable insulin pen comprises, similar to a reusable insulin pen, a cartridge containing insulin. The cartridge many times contains about 3 milliliter of insulin, which depending of the dosage will last a number of insulin treatments. When the cartridge is emptied the entire insulin pen is disposed. Regarding disposable devices the cartridge is either integrated in the insulin pen or assembled inside of the body of the insulin pen in such way that it can't be disouterd unless breaking the disposable device. An example of alternative assembly methods are regular non-dismountable snap-in-closure, which is designed in such way it can't be dismounted without breaking. Another example is to glue or weld the cartridge housing, which in most cases is made of plastic, to the insulin pen cover. An often used argument why a disposable device is better than a reusable devise is that the user doesn't have to get as much distressed about bacterial growth and that a disposable device can't be filled with another medicament than what it is intended for. Furthermore the mechanical platform can be simplified, as the plunger rod in almost all of these existing automatic devices for distribution of liquid drug can't reverse as they aren't equipped with a plunger rod clutch mechanism. Consequently the plunger rod moves ahead step by step, or in other words, dose by dose until the plunger rod has pushed the plunger towards the front end of the cartridge, and thus emptied all the medicament of the cartridge.

A reusable device is an automatic device for distribution of liquid medicament, where the cartridge (9) can be replaced when the medicament has run out. When the medicament has run out, the cartridge housing (18) is dismantled together with the empty cartridge (9) and it's belonging plunger (8). The cartridge (9) with its belonging plunger (8) is then replaced with a new similar one which is filled with liquid medicament. In the present embodiment of the invention the cartridge housing (18) is equipped with a threaded interface, which correspond to threads in the front cover. The user commonly has to reverse the plunger rod (19) by hand, but in the present embodiment of the invention the device is equipped with another clutch mechanism, which in it's front end is composed by teeth in the front cover (16) that correspond to teeth in the plunger rod clutch (6). As the cartridge housing (18) is screw fitted onto the front cover these teeth interlock each other and locks the plunger rod clutch (6).

In case the cartridge housing (18) has been equipped with a new cartridge (9) and is about to be screw fitted to the front cover the plunger rod return spring (17) separates the teeth from each other whereby the plunger rod clutch (6) can rotate freely. As a result of that the plunger rod clutch (6) can rotate freely, the plunger rod (19) is allowed to be pushed backwards in a backward spinning movement which is guided by the threaded hub of the planet carrier (5), pushed back by the plunger (8) which as the liquid medicament is to be more or less regarded as incompressible, until the cartridge housing (18) is screw fitted on to the front cover (16) and the teeth of the plunger rod clutch (6) and the front cover (16) are interlocked to each other again.

The invention claimed is:

1. An injection device, comprising: a drive shaft; a clutch adapted to engage the drive shaft; a plunger rod adapted to engage the clutch; a dose stop adapted to engage the clutch; a planetary gear mechanism adapted to engage the dose stop, the planetary gear mechanism includes a hole adapted to receive the plunger rod; and a trigger button adapted to selectively engage the dose stop.

2. The injection device according to claim 1, further comprising: a dose knob coupled to the drive shaft.

3. The injection device according to claim 2, further comprising: a dose drum coupled to the drive shaft, the dose drum having a first thread.

4. The injection device according to claim 3, further comprising: a rear cover including a second thread adapted to mate with the first thread of the dose drum.

5. The injection device according to claim 4, wherein rotation of the dose knob in a first direction causes rotation of the drive shaft in the first direction.

6. The injection device according to claim 5, wherein rotation of the drive shaft in the first direction causes rotation of the dose drum in the first direction relative to the rear cover.

7. The injection device according to claim 6, wherein rotation of the dose drum in the first direction relative to the rear cover causes the dose drum to move axially within the rear cover due to engagement of the first and second threads.

8. The injection device according to claim 7, further comprising: a dose drum spring biasing the dose drum in towards a front of the injection device, wherein the dose drum spring is compressed during axial movement of the dose drum relative to the rear cover when the dose drum is rotated in the first direction.

9. The injection device according to claim 8, wherein the clutch is adapted to allow rotation of the drive shaft in the first direction and the clutch is adapted to rotate in conjunction with the drive shaft when the drive shaft rotates in a second direction opposite the first direction.

10. The injection device according to claim 9, wherein rotation of the clutch causes rotation of the dose stop.

11. The injection device according to claim 10, wherein the engagement of the dose stop by the trigger button prevents rotation of the dose stop and the clutch in the second direction.

12. The injection device according to claim 11, wherein, when the trigger button disengages the dose stop, the dose drum is forced in a proximal direction relative to the rear cover by the biasing force of the dose drum spring, wherein the dose drum rotates in the second direction relative to the rear cover when the dose drum moves in the proximal direction relative to the rear cover.

13. The injection device according to claim 12, wherein rotation of the dose drum in the second direction causes the drive shaft and the clutch to rotate in the second direction.

14. The injection device according to claim 13, wherein rotation of the clutch in the second direction causes the plunger rod to rotate in the second direction.

15. The injection device according to claim 14, wherein rotation of the plunger rod in the second direction advances the plunger rod in a distal direction through the hole in the planetary gear mechanism due to a threaded engagement between the plunger rod and the hole.

16. The injection device according to claim 1, wherein the dose stop includes a sun gear adapted to engage the planetary gear mechanism.

17. The injection device according to claim 16, wherein the planetary gear mechanism includes a planet carrier including a plurality of planetary gears rotatably coupled to the planet carrier, the planetary gears adapted to engage the sun gear.

18. The injection device according to claim 17, further comprising: a front cover including a ring gear adapted to engage the planetary gears.

19. The injection device according to claim 1, further comprising: a clutch spring biasing the clutch in engagement with the drive shaft.

20. The injection device according to claim 1, further comprising: a trigger button spring biasing the trigger button in engagement with the dose stop.

* * * * *

UNITED STATES PATENT AND TRADEMARK OFFICE
CERTIFICATE OF CORRECTION

PATENT NO. : 8,663,167 B2 Page 1 of 1
APPLICATION NO. : 13/259473
DATED : March 4, 2014
INVENTOR(S) : Istvan Bartha It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 323 days.

Signed and Sealed this
Twenty-ninth Day of September, 2015

Michelle K. Lee
*Director of the United States Patent and Trademark Office*